Figure 1:
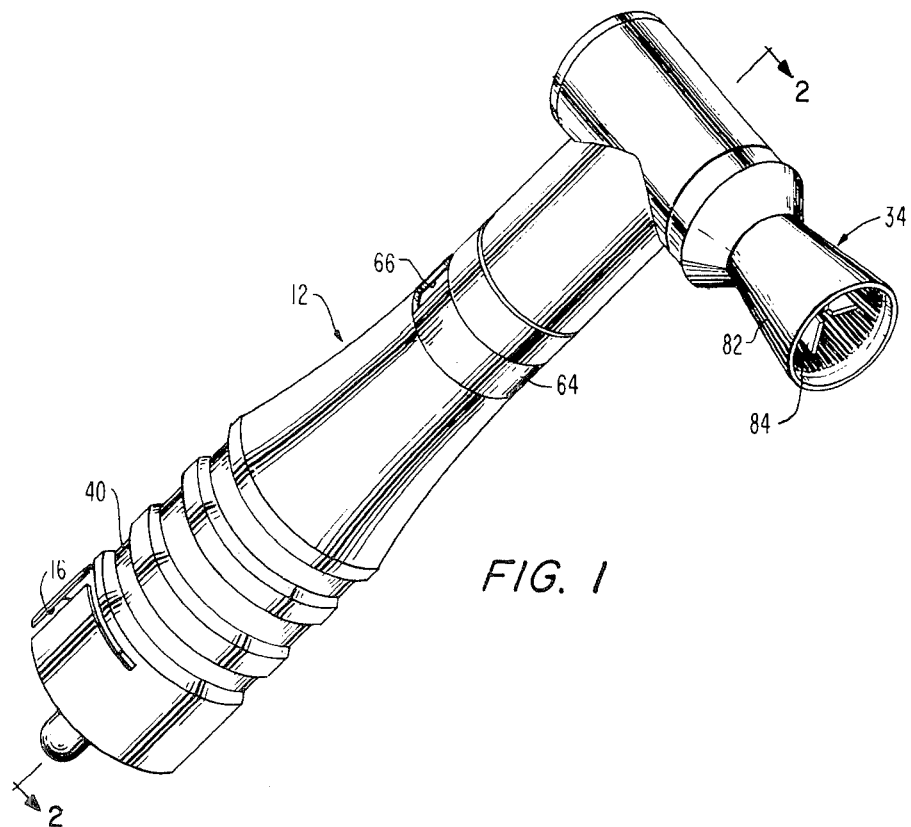

United States Patent [19]

Fisher et al.

[11] Patent Number: 4,486,175
[45] Date of Patent: Dec. 4, 1984

[54] DENTAL APPLIANCE

[75] Inventors: Leo Fisher, Denver; Atilla Weiser, Westminster, both of Colo.

[73] Assignee: Teledyne Industries, Inc.

[21] Appl. No.: 438,048

[22] Filed: Nov. 1, 1982

[51] Int. Cl.³ ............................................. A61C 1/02
[52] U.S. Cl. ................................. 433/104; 433/115; 433/133
[58] Field of Search .................... 433/104, 80, 82, 83, 433/85, 115

[56] References Cited

U.S. PATENT DOCUMENTS

| | | | |
|---|---|---|---|
| 2,098,317 | 11/1937 | Staunt | 433/104 |
| 2,504,233 | 4/1950 | Staunt | 433/115 |
| 3,389,468 | 6/1968 | Lewis et al. | 433/82 |

Primary Examiner—Robert Peshock
Attorney, Agent, or Firm—Hugh H. Drake

[57] ABSTRACT

A dental appliance has an elongated hollow tube within the interior of which is mounted for rotation an elongated drive shaft. One end of the tube is coupled to a handle as is the drive shaft which is driven from the handle in rotation. A head joined to the other end of the tube defines an interior cavity within which a hub is mounted for rotation about an axis disposed at an angle with respect to the drive shaft. Motion is translated from the drive shaft to the hub. An opening in the head enables the hub to be accessed through the opening. Included in the hub is a barrel section for securing a variety of dental attachments thereto. A seal is created between the opening from the cavity and the hub in order to prevent fluid flow therethrough. Lubricant is introduced within the tube and the drive shaft actuates an augar or the equivalent for propelling the lubricant into the motion translator.

4 Claims, 2 Drawing Figures

U.S. Patent   Dec. 4, 1984   4,486,175

DENTAL APPLIANCE

The present invention pertains to a dental appliance. More particularly, it relates to a prophylactic angle handpiece head, often called a "prophy angle"; it is attachable to a handpiece intended to be grasped by the dentist or other user.

Prophy angles are in constant use in the dental profession. They typically involve a hand held unit from which projects at a right angle a driving connection to which is attached a pumice cup, for enabling the polishing of the teeth, or some other device. Representative prior art will be found in U.S. Letters Pat. Nos. 3,407,502 and 3,478,433 issued to Richmond as well as in 4,053,983—Flatland and U.S. Pat. No. Des. 168,286 to Brown.

Mechanical power is delivered into the handpiece by means of either electrically or hydraulically derived force the development of which drives the ultimate applicator. The applicator often is simply a cup of resilient material within which the operator places a pumice for polishing the teeth. On other occasions, however, the unit may be used to drive a different kind of attachment.

A problem addressed in the aforesaid patents to Richmond is that of pumice creeping backwardly into the apparatus and adversely affecting bearings and internal gearing which are involved in order to allow translation of motion from one direction to another. The ultimate applicator usually is rotated about an axis which is at a right angle to the rotational axis of the driving source. The gearing and bearings employed for that purpose are highly subject to deterioration should any of the abrasive pumice find its way back into the assembly. Thus, a good seal is desired at the point of connection of the applicator back into the unit.

Assuming a good seal, however, another problem may develop. Because the devices involve rotation at substantial speeds, bearings and gears involved in the motion-translating apparatus from drive to delivery of forces tend to wear because of lack of lubrication. The prior art has not heretofore provided adequate means for assuring easy lubrication in a device, such as this, which must be used in or at least adjacent to a patient's mouth, while at the same accomodating sterilization.

It is, accordingly, a general object of the present invention to provide a new and improved prophy angle which overcomes deficiencies and difficulties in similar devices of the prior art.

Another object of the present invention is to provide a new and improved prophy angle which ensures proper lubrication of the mechanical components in a simple and unobtrusive manner.

Still another object is to provide a new and improved prophy angle which enables sterilization without necessitating disassembly.

A further object of the present invention is to provide a new and improved prophy angle which accomodates its improvements without undue increase in cost.

As presented, a dental appliance has an elongated hollow tube through which extends a drive shaft supported therewithin for axial rotation. One end of the tube is arranged for coupling to a handle which also couples one end of the drive shaft to a source of rotary power. A head, joined to the other end of the tube, defines an interior cavity within which there is mounted a hub for rotation about an axis disposed at an angle with respect to the shaft. Also disposed in connection with the cavity is motion translating means that convey rotory force from the shaft to the hub. An opening defined in the head and leading outwardly from the cavity allows the hub to be accessed. Defined in the hub is a securement for a dental attachment which extends outwardly. A seal is created between the opening and the hub in order to inhibit fluid flow therethrough. Also included in the appliance are means for introducing a lubricant effectively within the tube as well as means actuated by the drive shaft for propelling that lubricant into the motion translating means.

Figure 2:
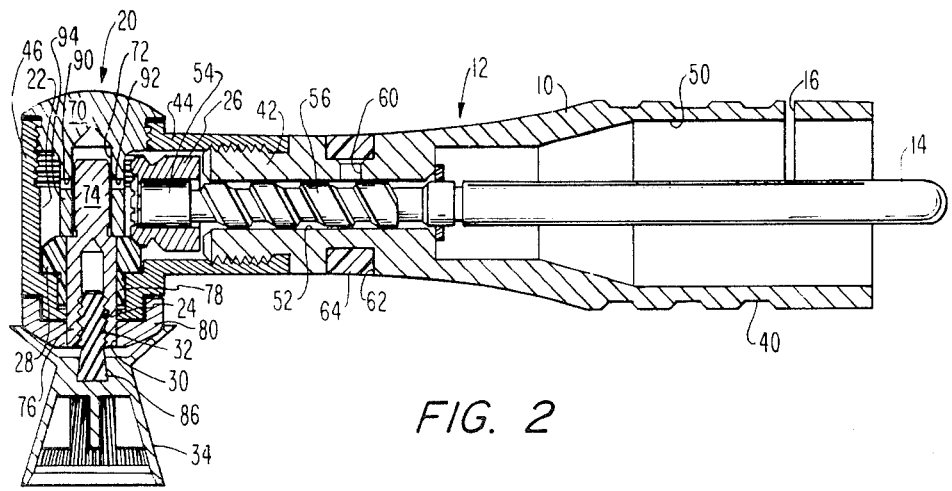

The features of the present invention which are believed to be patentable are set forth with particularity in the appended claims. The organization and manner of operation of the invention, together with further objects and advantages thereof, may best be understood by reference to the following description taken in connection with the accompanying drawings in the several figures of which like reference numerals identify like elements, and in which:

FIG. 1 is an isometric view of a dental appliance; and
FIG. 2 is a cross-sectional view taken longitudinally through the appliance of FIG. 1.

An elongated hollow tube 10 in a dental appliance 12 encompasses an elongated drive shaft 14 supported within tube 10 for axial rotation. At one end of tube 10 is a modified bayonet coupling which interfits with a conventional handle (not shown) that connects to and effects rotation of shaft 14. The rotational power source may ultimately be driven, as is conventional, either by air or by electric motor. In this case, appliance 12 is arranged to fit onto a belt or air-driven round-nose doriot handpiece. The handpiece preferably is operated to drive shaft 14 at about 3500 revolutions per minute.

Joined to the other end of tube 10 is a head 20 which defines an interior cavity 22. A hub 24 is mounted in cavity 22 for rotation about an axis disposed at an angle with respect to shaft 14. In this case, that angle is 90 degrees, because this appears from experience to be that preferred by the users. However, it could be a different angle.

Gears 26 and 28 transmit rotory motion from drive shaft 14 to hub 24. An opening 30 is defined in head 20 and leads outwardly from cavity 22, so that a portion of hub 24 effectively projects through opening 30. Defined within hub 24 is a threaded segment 32 for a dental attachment 34.

In more detail, tube 10 includes external corrugations 40 near coupling 16 to aid the user in fitting the unit to the handpiece or handle. The external diameter of tube 10 then decreases smoothly to a necked down snout 42 threaded to receive a neck 44 that integrally continues into a head shell 46 in which cavity 22 is formed. Tube 10 has an enlarged chamber 50 in its rear portion and forward of which is defined a narrower bore 52.

Drive shaft 14 is disposed through chamber 50 and bore 52, terminating in a nose 54 upon which pinion gear 26 is rigidly affixed. Behind nose 54, within bore 52, shaft 14 is shaped to define an auger 56 that has a left-hand lead. Auger 56 has wide lands which serve in bore 52 as the bearing for shaft 14.

At the rear of auger 56, shaft 14 is grooved to define a gland at that end of bore 52. A resilient "E" ring seats in place to create a fluid seal between bore 52 and chamber 50.

Intermediate the length of auger 56, a lubricating aperture 60 opens through the wall of tube 10 into bore 52 from an external channel 62. Seated in channel 62 is a ring cover 64 which is continuous except for a gap 66. Rotation of ring cover 64 permits selective opening or closing of aperture 60.

A bearing cap 70 is threaded into the top of shell 46 and centrally defines another bore 72 in which is seated a shank 74 on the upper end portion of hub 24. The lower end portion of hub 24 is a barrel 76 in which threaded segment 32 is formed. Rigidly secured on barrel 76 is bevel gear 28 which includes a skirt 78 that rides within a correspondingly necked down lower portion of cavity 22. On the lower end of barrel 76 is secured a slinger cup 80, the lower end of shell 46 being shaped to mate therewith.

Mounted to hub 24, in this case, is a conventional prophy cup 34. It is formed of a soft, flexible rubber or the like and includes a sidewall 82 in the shape of a truncated cone and has internal crossed vanes 84. Captivated in the top of cup 34 is a screw 86 that mates into threaded segment 32.

While prophy cups are conventional, various ones differ in thread pitch. To accomodate variation, segment 32 first is tapped at sixty-four threads per inch under standard UNC-2B. The segment is then re-tapped at seventy-two threads per inch under standard UNF-2B. This combination appears to allow mounting of a variety of different cups that are available.

Slinger 80 is spaced slightly below shell 46 to leave a maze-like circumferential passage. Pumice tending to creep upwardly, internally or exteriorly, is slung laterally and inhibited from entering the bearing and gear structure. Also, skirt 78 assists in defining a further maze as against upward creep.

To lubricate the unit, ring 64 is turned to expose aperture 60. Preferably using a squeeze bottle containing the lubricant, its nozzle is inserted into aperture 60, and the bottle is squeezed while operating the unit in the normal clockwise direction until excess is expelled from the head area. The flow of lubrication into head 20 is enabled by at least one of a pair of holes 90 and 92 which open into cavity 72 through a skirt 94 of cap 70. After retracting that excess by turning shaft 14 briefly in the counter-clockwise direction, ring 64 is turned to close aperture 60 and the unit is wiped clean.

Before removing a prophy cup, it is recommended that the entire unit be rinsed with hot running water. Thereafter, the appliance may be autoclaved, either dry heat or gaseous sterilization. With the instant approach, lubrication is not required after each autoclaving. Thorough and even lubrication always are assured and, yet, both autoclaving and lubrication are accomplished without need for any disassembly.

While a particular embodiment of the invention has been shown and described, it will be obvious to those skilled in the art that changes and modifications may be made without departing from the invention in its broader aspects. Therefore, the aim in the appended claims is to cover all such changes and modifications as fall within the true spirit and scope of that which is patentable.

We claim:

1. A dental handpiece comprising:
   an elongated hollow tube;
   an elongated drive shaft supported within said tube for axial rotation;
   means for coupling one end of said tube to a handle and for coupling one end of said shaft to a source of rotary power;
   a head joined to the other end of said tube and defining an interior cavity;
   a hub mounted in said cavity for rotation about an axis disposed at an angle with respect to said shaft;
   motion translating means disposed in connection with said cavity for transmitting rotary force from said shaft to said hub;
   an opening defined in said head and leading outwardly from said cavity, a portion of said hub being accessible through said opening;
   means effectively defined in said hub for securing a dental attachment thereto in a location beyond said opening from said cavity;
   means for creating a seal between said opening and said hub in order to prevent fluid flow therethrough;
   means for introducing a lubricant effectively within said tube; and
   means actuated by said shaft for propelling said lubricant into said motion translating means.

2. An handpiece as defined in claim 1 in which said propelling means is an auger defined on said drive shaft.

3. A handpiece as in claim 1 in which said propelling means constitutes a bearing for said drive shaft in association with said motion translating means.

4. A handpiece as in claim 1 in which said securing means includes a threaded segment, said segment defining at least a pair of respectively different thread patterns.

* * * * *